US007619136B2

(12) United States Patent
Tasaka et al.

(10) Patent No.: US 7,619,136 B2
(45) Date of Patent: Nov. 17, 2009

(54) TECHNIQUE FOR EXTENDING BIOLOGICAL SUGAR CHAIN VIA INTRODUCTION OF GLYCOSYLTRANSFERASE GENE

(75) Inventors: Yasushi Tasaka, Sapporo (JP); Takeshi Matsumura, Sapporo (JP); Kouki Matsuo, Sapporo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/396,720

(22) Filed: Apr. 4, 2006

(65) Prior Publication Data

US 2006/0288456 A1 Dec. 21, 2006

(30) Foreign Application Priority Data

Apr. 5, 2005 (JP) ............................ 2005-109277

(51) Int. Cl.
*C12N 15/82* (2006.01)
*A01H 5/00* (2006.01)

(52) U.S. Cl. ....................... 800/288; 800/298; 435/419; 435/468

(58) Field of Classification Search ....................... None
See application file for complete search history.

(56) References Cited

U.S. PATENT DOCUMENTS

| | | | | |
|---|---|---|---|---|
| 5,294,593 | A * | 3/1994 | Khan | 504/100 |
| 6,783,966 | B1 | 8/2004 | Kojima et al. | |
| 7,115,404 | B2 * | 10/2006 | Clausen et al. | 435/193 |

FOREIGN PATENT DOCUMENTS

| | | |
|---|---|---|
| JP | 10-295371 | 10/1998 |
| JP | 2003-535965 | 12/2003 |
| WO | WO 0131045 | 5/2001 |
| WO | WO 0159079 | 8/2001 |
| WO | WO 2006025443 | 3/2006 |

OTHER PUBLICATIONS

Webster's online dictionary; definition of "potency"; http://dictionary.reference.com/browse/potency, pp. 1-2.*
Weibauer et al. Nuclear pre-mRNA processing in plants: distinct modes of 3'-splice-site selection in plants and animals. (1988) MCB, vol. 8, pp. 2042-2051.*
Nomura et al. Purification, cDNA cloning, and expression of UDP-Gal: glucosylceramide beta-1,4-galactosyltransferase from rat brain. (1998) JBC, vol. 273, pp. 13570-13577.*
Rosin L. J. Transgenic Plants Bio-Farming for the Future (2004) Chapter Five in "Bioprocess International"; publisher: BioProcess International, Westborough, MA; pp. 52-54, 56, 58, 60, and 61.*
Takizawa et al. cDNA cloning anad expression of human lactosylceramide synthase. (1999) Biochimica et Biophysica Acta; vol. 1438; pp. 301-304.*
Keusch et al. (2000) "Cloning of Gb3 Synthase, the Key Enzyme in Globo-series Glycosphingolipid Synthesis, Predicts a Family of α1,4-Glycosyltrasferases Conserved in Plants, Insects and Mammals" J. Biol. Chem. 275(33):25315-25321.
Palacpac et al. (1999) "Stable Expression of Human β1,4-Galactosyltransferase in Plant Cells Modifies N-Linked Glycosylation Patterns" PNAS 96:4692-4697.

* cited by examiner

*Primary Examiner*—Cathy Kingdon Worley
(74) *Attorney, Agent, or Firm*—Suzannah K. Sundby, Esq.; Smith, Gambrell & Russell, LLP (57) ABSTRACT

Disclosed herein is a method for extending the sugar chain modification of a lipid or a protein by introducing two or more glycosyltransferase genes in a biological organism (including animal-, plant- or microbial cells). Also disclosed is a recombinant plant with a potency to generate ceramide trihexoside and a method for generating ceramide trihexoside using the plant. Methods for synthetically preparing ceramide trihexoside utilizing a transgenic tobacco prepared by constructing an expression vector with the ORF of human- or animal-derived α1,4-galactosyltransferase gene (α1,4 GT) for plants and subsequently introducing the vector into tobacco using a genetic approach for plants and methods for the mass-scale production of ceramide trihexoside are also disclosed herein.

18 Claims, 8 Drawing Sheets

FIG. 1

←1062 bps

```
ATG TCC AAG CCC CCC GAC CTC CTG CTG CGG CTG CTC CGG GGC GCC CCA    48
Met Ser Lys Pro Pro Asp Leu Leu Leu Arg Leu Leu Arg Gly Ala Pro
1               5                   10                  15

AGG CAG CGG GTC TGC ACC CTG TTC ATC ATC GGC TTC AAG TTC ACG TTT    96
Arg Gln Arg Val Cys Thr Leu Phe Ile Ile Gly Phe Lys Phe Thr Phe
                20                  25                  30

TTC GTC TCC ATC ATG ATC TAC TGG CAC GTT GTG GGA GAG CCC AAG GAG   144
Phe Val Ser Ile Met Ile Tyr Trp His Val Val Gly Glu Pro Lys Glu
            35                  40                  45

AAA GGG CAG CTC TAT AAC CTG CCA GCA GAG ATC CCC TGC CCC ACC TTG   192
Lys Gly Gln Leu Tyr Asn Leu Pro Ala Glu Ile Pro Cys Pro Thr Leu
50                  55                  60

ACA CCC CCC ACC CCA CCC TCC CAC GGC CCC ACT CCA GGC AAC ATC TTC   240
Thr Pro Pro Thr Pro Pro Ser His Gly Pro Thr Pro Gly Asn Ile Phe
65                  70                  75                  80

TTC CTG GAG ACT TCA GAC CGG ACC AAC CCC AAC TTC CTG TTC ATG TGC   288
Phe Leu Glu Thr Ser Asp Arg Thr Asn Pro Asn Phe Leu Phe Met Cys
                85                  90                  95

TCG GTG GAG TCG GCC GCC AGA ACT CAC CCC GAA TCC CAC GTG CTG GTC   336
Ser Val Glu Ser Ala Ala Arg Thr His Pro Glu Ser His Val Leu Val
            100                 105                 110

CTG ATG AAA GGG CTT CCG GGT GGC AAC GCC TCT CTG CCC CGG CAC CTG   384
Leu Met Lys Gly Leu Pro Gly Gly Asn Ala Ser Leu Pro Arg His Leu
        115                 120                 125

GGC ATC TCA CTT CTG AGC TGC TTC CCG AAT GTC CAG ATG CTC CCG CTG   432
Gly Ile Ser Leu Leu Ser Cys Phe Pro Asn Val Gln Met Leu Pro Leu
    130                 135                 140

GAC CTG CGG GAG CTG TTC CGG GAC ACA CCC CTG GCC GAC TGG TAC GCG   480
Asp Leu Arg Glu Leu Phe Arg Asp Thr Pro Leu Ala Asp Trp Tyr Ala
145                 150                 155                 160

GCC GTG CAG GGG CGC TGG GAG CCC TAC CTG CTG CCC GTG CTC TCC GAC   528
Ala Val Gln Gly Arg Trp Glu Pro Tyr Leu Leu Pro Val Leu Ser Asp
                165                 170                 175

GCC TCC AGG ATC GCA CTC ATG TGG AAG TTC GGC GGC ATC TAC CTG GAC   576
Ala Ser Arg Ile Ala Leu Met Trp Lys Phe Gly Gly Ile Tyr Leu Asp
            180                 185                 190

ACG GAC TTC ATT GTT CTC AAG AAC CTG CGG AAC CTG ACC AAC GTG CTG   624
Thr Asp Phe Ile Val Leu Lys Asn Leu Arg Asn Leu Thr Asn Val Leu
        195                 200                 205

GGC ACC CAG TCC CGC TAC GTC CTC AAC GGC GCG TTC CTG GCC TTC GAG   672
Gly Thr Gln Ser Arg Tyr Val Leu Asn Gly Ala Phe Leu Ala Phe Glu
    210                 215                 220

CGC CGG CAC GAG TTC ATG GCG CTG TGC ATG CGG GAC TTC GTG GAC CAC   720
Arg Arg His Glu Phe Met Ala Leu Cys Met Arg Asp Phe Val Asp His
225                 230                 235                 240
```

FIG. 8

```
TAC AAC GGC TGG ATC TGG GGT CAC CAG GGC CCG CAG CTG CTC ACG CGG      768
Tyr Asn Gly Trp Ile Trp Gly His Gln Gly Pro Gln Leu Leu Thr Arg
                245             250                 255

GTC TTC AAG AAG TGG TGT TCC ATC CGC AGC CTG GCC GAG AGC CGC GCC      816
Val Phe Lys Lys Trp Cys Ser Ile Arg Ser Leu Ala Glu Ser Arg Ala
                260             265                 270

TGC CGC GGC GTC ACC ACC CTG CCC CCT GAG GCC TTC TAC CCC ATC CCC      864
Cys Arg Gly Val Thr Thr Leu Pro Pro Glu Ala Phe Tyr Pro Ile Pro
            275             280                 285

TGG CAG GAC TGG AAG AAG TAC TTT GAG GAC ATC AAC CCG GAG GAG CTG      912
Trp Gln Asp Trp Lys Lys Tyr Phe Glu Asp Ile Asn Pro Glu Glu Leu
        290             295             300

CCG CGG CTG CTC AGT GCC ACC TAT GCT GTC CAC GTG TGG AAC AAG AAG      960
Pro Arg Leu Leu Ser Ala Thr Tyr Ala Val His Val Trp Asn Lys Lys
305             310             315                 320

AGC CAG GGC ACG CGG TTC GAG GCC ACG TCC AGG GCA CTG CTG GCC CAG     1008
Ser Gln Gly Thr Arg Phe Glu Ala Thr Ser Arg Ala Leu Leu Ala Gln
                325             330                 335

CTG CAT GCC CGC TAC TGC CCC ACG ACG CAC GAG GCC ATG AAA ATG TAC     1056
Leu His Ala Arg Tyr Cys Pro Thr Thr His Glu Ala Met Lys Met Tyr
            340             345                 350

TTG TGA                                                             1062
Leu
353
```

FIG. 8 CONT'D

```
Met Ser Lys Pro Pro Asp Leu Leu Leu Arg Leu Leu Arg Gly Ala Pro
 1           5                   10                  15

Arg Gln Arg Val Cys Thr Leu Phe Ile Ile Gly Phe Lys Phe Thr Phe
             20                  25                  30

Phe Val Ser Ile Met Ile Tyr Trp His Val Val Gly Glu Pro Lys Glu
         35                  40                  45

Lys Gly Gln Leu Tyr Asn Leu Pro Ala Glu Ile Pro Cys Pro Thr Leu
     50                  55                  60

Thr Pro Pro Thr Pro Pro Ser His Gly Pro Thr Pro Gly Asn Ile Phe
 65              70                  75                      80

Phe Leu Glu Thr Ser Asp Arg Thr Asn Pro Asn Phe Leu Phe Met Cys
                 85                  90                  95

Ser Val Glu Ser Ala Ala Arg Thr His Pro Glu Ser His Val Leu Val
             100                 105                 110

Leu Met Lys Gly Leu Pro Gly Gly Asn Ala Ser Leu Pro Arg His Leu
         115                 120                 125

Gly Ile Ser Leu Leu Ser Cys Phe Pro Asn Val Gln Met Leu Pro Leu
     130                 135                 140

Asp Leu Arg Glu Leu Phe Arg Asp Thr Pro Leu Ala Asp Trp Tyr Ala
145                 150                 155                 160

Ala Val Gln Gly Arg Trp Glu Pro Tyr Leu Leu Pro Val Leu Ser Asp
                 165                 170                 175

Ala Ser Arg Ile Ala Leu Met Trp Lys Phe Gly Gly Ile Tyr Leu Asp
             180                 185                 190

Thr Asp Phe Ile Val Leu Lys Asn Leu Arg Asn Leu Thr Asn Val Leu
         195                 200                 205

Gly Thr Gln Ser Arg Tyr Val Leu Asn Gly Ala Phe Leu Ala Phe Glu
     210                 215                 220

Arg Arg His Glu Phe Met Ala Leu Cys Met Arg Asp Phe Val Asp His
225                 230                 235                 240

Tyr Asn Gly Trp Ile Trp Gly His Gln Gly Pro Gln Leu Leu Thr Arg
                 245                 250                 255
```

FIG. 9

```
Val Phe Lys Lys Trp Cys Ser Ile Arg Ser Leu Ala Glu Ser Arg Ala
            260             265             270

Cys Arg Gly Val Thr Thr Leu Pro Pro Glu Ala Phe Tyr Pro Ile Pro
        275             280             285

Trp Gln Asp Trp Lys Lys Tyr Phe Glu Asp Ile Asn Pro Glu Glu Leu
        290             295             300

Pro Arg Leu Leu Ser Ala Thr Tyr Ala Val His Val Trp Asn Lys Lys
305             310             315             320

Ser Gln Gly Thr Arg Phe Glu Ala Thr Ser Arg Ala Leu Leu Ala Gln
            325             330             335

Leu His Ala Arg Tyr Cys Pro Thr Thr His Glu Ala Met Lys Met Tyr
            340             345             350

Leu
353
```

FIG. 9 CONT'D

TECHNIQUE FOR EXTENDING BIOLOGICAL SUGAR CHAIN VIA INTRODUCTION OF GLYCOSYLTRANSFERASE GENE

CROSS REFERENCE TO RELATED APPLICATIONS

This application claims the benefit Japanese Patent Application Serial No. JP 2005-109277, filed 5 Apr. 2005, which is herein incorporated by reference in its entirety.

BACKGROUND OF THE INVENTION

1. Field of the Invention

The present invention relates to a transgenic plant with glycosyltransferase gene introduced therein, and the use thereof. More specifically, the invention relates to a technique for synthetically preparing a lipid or a protein with a sugar chain modification intrinsic to animals at a state completely free of any risk of animal-derived infections, in a biological organism such as plant. In accordance with the invention, it is provided a technique for extending the biological sugar chain of a lipid or a protein in animal-, plant- and microbial cells via the introduction of glycosyltransferase gene.

2. Description of the Related Art

Sphingoglycolipids of animal type are utilized as chemical agents for raw materials of pharmaceutical products and cosmetics. Additionally because the sugar chain thereof works as a receptor for various viruses such as influenza virus and bacteria toxins (Karlson, K. A. Animal glycosphingolipids as membrane attachment site for bacteria, Ann. Rev. Biochem., 58, 309-350, 1989), practical application of sphingoglycolipids as novel therapeutic agents with no content of antibiotics or synthetic drug substances has been desired against these infections at an early stage (Tokuhyo 2003-535965, Tokuhyo Hei 10-50347). It is known for example that ceramide trihexoside is a receptor for vero toxin (the toxin generated by *Escherichia coli* O-157) and Shiga Toxin (the toxin generated by Shigella) for their binding onto cell surface (Cohen, A., Hannigan G E, Williams B R, Lingwood C A, J. Biol. Chem., Dec. 15, 1987; 262(35): 17088-91. Related Articles, Links Roles of globotriosyl- and galabiosylceramide in vero toxin binding and high affinity interferon receptor; Lindberg, A A, Brown J E, Stromberg N, Westling-Ryd M, Schultz J E, Karlsson K A, J. Biol. Chem., Feb. 5, 1987; 262(4): 1779-85. Related Articles, Links Identification of the carbohydrate receptor for Shiga toxin produced by Shigella dysenteriae type I.)

The research works of Watarai, et al. (Watarai, S. et al. Inhibition of vero cell cytotoxic activity in *Escherichia coli* 0157: H7 lysates by globotriaosylceramide, Gb3, from bovine milk. Biosci. Biotechnol. Biochem., 65, 414-419 (2001)) indicate that bovine-derived ceramide trihexoside added to a culture cell traps vero toxin to inhibit the binding of the toxin to the cell so that vero toxin is inactivated. This indicates a possibility of the pharmaceutical application of ceramide trihexoside. Ceramide trihexoside is abundant in animal tissues (in brain, in particular). However, the related-art method of the extraction thereof from animal tissues is problematic because of infections such as BSE (bovine spongiform encephalopathy). This can be prepared synthetically by an artificial method. However, the method is tough and highly costly. Thus, the method is disadvantageously inappropriate for the mass-scale production thereof (Hasegawa, A., Morita, M., Kojima, Y., Ishida, H. & Kiso, M., Synthesis of cerebroside, lactosylceramide, and ganglioside GM3 analogs containing β-thioglycosidically linked ceramide. Carbonhydr. Res., 214, 43-53 (1991)).

Various reports tell about research examples of the production of useful substances using genetic recombinant plants (Voelker, T. A. et al.: Fatty acid biosynthesis redirected to medium chains in transgenic oil seed plants, Science, 257, 72-74 (1992); Sayanova, O. et al.: Expression of a borage desaturase cDNA containing an N-terminal cytochrome b5 domain results in the accumulation of high levels of Δ6-desaturated fatty acids in transgenic tobacco, Proc. Natl. Acad. Sci. U.S.A., 94, 4211-4216 (1997); Ye, X. et al.: Engineering the provitamin A (β-carotene) biosynthetic pathway into (carotenoid-free) rice endosperm, Science, 287, 303-305 (2000); Datta, K.: Bioengineered 'golden' indica rice cultivars with β-carotene methabolism in the endosperm with hygromycin and mannose selection systems, Plant Biotech. J., 1, 81-90 (2003); Tozawa, Y. et al.: Characterization of rice anthranilate synthase α-subunit genes OASA 1 and OASA2. Tryptophan accumulation in transgenic rice expressing a feedback-insensitive mutant of OASA1, Plant Physiology, 126, 1493-1506 (2001)). Such types of methods are advantageously low in cost with no generation of carbon dioxide, causing no concerns of any risk of animal infections.

Ceramide trihexoside is one of biosynthetic products of sphingoglycolipids with various physiological activities. It is shown that ceramide trihexoside can synthetically be prepared from the precursor lactosylceramide via the glycosyl transfer of α1,4-galactosyltransferase (α1,4GT) (JP-A-10-295371). The inventors previously produced a transgenic tobacco generating lactosylceramide via the introduction of human β1,4-galactosyltransferase (β1,4GT5). Because the plant lacks the α1,4 GT gene, the plant cannot produce ceramide trihexoside. This is discussed in co-pending International Patent Application number PCT/JP2005/015899 (Publication No. WO 2006/025443).

A research example is reported, where only one hβ-1,4-GalT 1 (accession No. X55415 or X13223) as an isozyme of β1,4GT is introduced in a liquid culture cell of tobacco, to transfer galactose into the protein (Nirianne Q. Palacpac et al., Stable expression of human β1,4-galactosyl transferase in plant cells modifies N-linked glycosylation patterns, Proc. Natl. Acad. Sci. USA, 96, 4692-4697 (1999)). However, no example about glycosyl transfer into lipid is shown.

SUMMARY OF THE INVENTION

In such circumstances and in account of the related art, the inventors made investigations for the purpose of developing a technique for synthetically preparing a lipid or a protein with a sugar chain modification intrinsic to animals which is completely free of any risk of animal-derived infections and on a mass scale. The inventors found that the intended purpose could be attained by utilizing a transformed cell with two or more glycosyltransferase genes introduced therein and the like. Thus, the invention has been achieved. It is an object of the invention to provide a technique for extending a biological sugar chain to generate a lipid or a protein with a sugar chain modification in a biological organism. Additionally, it is an object of the invention to provide a method for synthetically preparing ceramide trihexoside as a glycolipid intrinsic to animals at a safe state completely free of any risk of animal-derived infections at a mass scale. Specifically, it is an object of the invention to provide a recombinant plant with a potency to generate ceramide trihexoside and a method for generating ceramide trihexoside using the plant. Still further, it is an object of the invention to provide a method for giving a sugar chain modification not essentially imparted to cells to a lipid and a protein, using an approach for introducing two or more glycosyltransferase genes into the cells.

So as to attain the objects, the invention comprises the following technical aspects.

(1) A vector comprising human- or animal-derived DNA described below in any one of (a) to (c):
(a) DNA encoding a protein of the amino acid sequence represented by SEQ ID NO: 2,
(b) DNA comprising the coding region in the nucleotide sequence represented by SEQ ID NO: 1; and
(c) DNA encoding a protein comprising an amino acid sequence with the substitution, deletion, addition and/or insertion of one or plural amino acids in the amino acid sequence represented by SEQ ID NO: 2,
downstream of a promoter region expressible in an animal-, plant- or microbial cell.
(2) A transgenic plant cell with two or more plural glycosyltransferase genes introduced therein and with a possibility of regenerating a plant with a potency to generate ceramide trihexoside.
(3) A transgenic plant cell described above in (2), where the human- or animal-derived β1,4-galactosyltransferase gene and the α1,4-galactosyltransferase gene are introduced.
(4) A plant with a potency to generate ceramide trihexoside as regenerated from the transgenic plant cell described above in (2) or (3).
(5) A plant with a potency to generate ceramide trihexoside, which is a progeny of the plant described above in (4) or a clone thereof.
(6) A reproduction material of a plant with a potency to generate ceramide trihexoside described above in (4) or (5).
(7) A method for producing a plant with a potency to generate ceramide trihexoside, including
(a) a step of introducing the vector described above in (1) into a plant cell, and
(b) a step of regenerating a plant from a transgenic plant cell with the vector introduced therein.
(8) A method for producing ceramide trihexoside including growing the plant described above in (4) or (5) to synthetically prepare ceramide trihexoside.
(9) A method for extending the sugar chain modification of a lipid or a protein by utilizing a transformed cell with two or more glycosyltransferase genes introduced into the cell or a plant regenerated from the cell.
(10) The method described above in (9), including utilizing a transformed cell with human- or animal-derived β1,4-galactosyltransferase gene and α1,4-galactosyltransferase gene introduced therein or utilizing a plant regenerated from the cell.
(11) The method described above in (9) or (10), where the cell is an animal-, plant- or microbial cell.

BRIEF DESCRIPTION OF THE DRAWINS

FIG. 1 is a view of the T-DNA region of pIG121Hm/α14GT. In the figure, $Hyg^R$ represents hygromycin-resistant gene; $Km^R$ represents kanamycin-resistant gene. P35S represents CaMV 35S promoter. Tnos represents the polyadenylation region of nopalin synthase.

FIG. 4 is a TLC picture of total lipid of tobacco leaves. 1 represents glycosyl ceramide standard sample (derived from cow); 2 represents sterylglucoside standard sample (derived from soybean); 3 represents lactosylceramide standard sample (derived from cow); 4 represents ceramide trihexoside standard sample (derived from cow); 5 represents wild tobacco strain; 6 represents β14GT5 gene-introduced tobacco (lactosylceramide-generating tobacco); 7 represents α14GT gene-introduced tobacco(ceramide trihexoside-generating tobacco); MGDG represents monogalactosyldiacylglycerol; SteGlc represents sterylglucoside; GlcCer represents glucosylceramide; DGDG represents digalactosyldiacylglycerol; LacCe represents lactosylceramide; SQDG represents sulfoquinobosyldiacylglycerol; oligoGDG represents oligogalactosyldiacylglycerol; CTH represents ceramide trihexoside.

FIG. 5 is a TLC picture of an alkali-resistant lipid of tobacco leaves. 1 represents glycosylceramide standard sample (derived from cow); 2 represents sterylglucoside standard sample (derived from soybean); 3 represents lactosylceramide standard sample (derived from cow); 4 represents ceramide trihexoside standard sample (derived from cow); 5 represents wild tobacco strain; 6 represents β14GT5 gene-introduced tobacco (lactosylceramide-generating tobacco); 7 represents α14GT gene-introduced tobacco(ceramide trihexoside-generating tobacco); MGDG represents monogalactosyldiacylglycerol; SteGlc represents sterylglucoside; GlcCer represents glucosylceramide; DGDG represents digalactosyldiacylglycerol; LacCer represents lactosylceramide; SQDG represents sulfoquinobosyldiacylglycerol; oligoGDG represents oligogalactosyldiacylglycerol; CTH represents ceramide trihexoside.

DETAILED DESCRIPTION OF THE INVENTION

The invention is now described below in more detail.

The inventors made attempts to generate ceramide trihexoside by introducing the cDNA of human-derived α1,4-galactosyltransferase (α1,4 GT) into the lactosylceramide-generating tobacco plant previously prepared by the inventors themselves. Consequently, the inventors detected ceramide trihexoside from a selected recombinant tobacco leaves. The amount was about 66 µg per 1 g of the selected recombinant tobacco leaves. Specifically, the introduction of α1,4 GT derived from humans enabled the mass-scale production of ceramide trihexoside in the recombinant plant.

The invention relates to providing a method for extending the sugar chain modification of a lipid or a protein by introducing two or more glycosyltransferase genes in a biological organism (including animal-, plant- or microbial cells), specifically providing a recombinant plant with a potency to generate ceramide trihexoside and a method for generating ceramide trihexoside using the plant.

The present invention further relates to synthetically preparing ceramide trihexoside utilizing a transgenic tobacco prepared by constructing an expression vector with the ORF of human- or animal-derived α1,4-galactosyltransferase gene (α1,4GT) for plants and subsequently introducing the vector into tobacco using a genetic approach for plants.

The present invention enables the mass-scale production of ceramide trihexoside using the recombinant plant.

In accordance with the invention, it is provided a vector carrying the coding region of a human- or animal-derived α1,4-galactosyltransferase gene (α1,4GT) and being expressible in an animal-, plant- or microbial cell, specifically a vector with DNA encoding human- or animal-derived α1,4 GT as functionally attached therein downstream a promoter region expressible in an animal-, plant- or microbial cell. The cDNA sequence (1062 bps) of α1,4 GT is shown in SEQ ID NO: 1, while the protein (353 amino acids) encoded by the DNA is shown as SEQ ID NO: 2.

The coding region of α1,4GT carried in the vector of the invention is preferably the cDNA sequence of α1,4 GT. cDNA can be prepared by routine methods for a person skilled in the art. Designing an appropriate pair of primers based on known nucleotide sequence information of α1,4GT for PCR using mRNA prepared from humans or animals as template and screening cDNA libraries by using generated amplified DNA fragments as probes, cDNA of α1,4GT can be prepared. The intended DNA can be prepared synthetically by using a commercially available DNA synthesizer.

As the DNA carried in the vector of the invention, any DNA with a potency to act on lactosylceramide and to synthetically prepare ceramide trihexoside via glycosyl transfer reaction can be used, including for example DNA (for example, mutants, derivatives, alleles, variants and homologs) encoding a protein structurally similar to α1,4 GT derived from humans (SEQ ID NO: 2). Such DNA includes for example DNA encoding a protein of an amino acid sequence with the substitution, deletion, addition and/or insertion of one or plural amino acids in the amino acid sequence represented by SEQ ID NO: 2.

A method well known to a person skilled in the art for preparing DNA encoding a protein of a modified amino acid sequence includes for example site-directed mutagenesis (Kramer, W. & Fritz, H.-J. (1987) Oligonucleotide-directed construction of mutagenesis via gapped duplex DNA. Methods in Enzymology, 154: 350-367). Additionally, amino acid mutations of proteins encoded by a nucleotide sequence via the mutation thereof may possibly occur in the natural kingdom. As described above, even DNA encoding a protein of an amino acid sequence with the substitution, deletion, addition and/or insertion of one or plural amino acids in the amino acid sequence (SEQ ID NO: 2) encoding α-1,4GT of naturally occurring type can be included in the DNA of the invention as long as the DNA can encode a protein with the same functions as those of the protein of naturally occurring type.

The number of amino acids to be modified is with no specific limitation, as long as the protein resulting from the modification reacts with lactosylceramide and has a potency to synthetically prepare ceramide trihexoside via glycosyl transfer reaction. Generally, the number of such amino acids is within 50, preferably 30, more preferably 10 amino acids (for example, within five amino acids, within three amino acids). The modification of amino acids is preferably done via preservative substitution. The numerical figures of the hydropathic index (Kyte and Doolittle, (1982) J. Mol. Biol., May 5, 1982; 157(1): 105-32) and the hydrophilicity value (U.S. Pat. No. 4,554,101) for the respective amino acids before and after the modification are preferably within ±2, more preferably within ±1, and most preferably within ±0.5. Even when the nucleotide sequence is mutated without any mutation of the amino acids in the protein (degenerate mutation), additionally, the resulting degenerate mutant is also included in the DNA of the invention.

Whether or not a protein encoded by a certain DNA "has a potency to react with lactosylceramide to synthetically prepare ceramide trihexoside via glycosyl transfer reaction" can be determined by introducing a vector carrying DNA encoding a mutant protein into a plant cell to synthetically prepare ceramide trihexoside from the lactosylceramide inherent to the introduced cell. As described below in Examples 6 through 10, for example, it can be determined by the presence or absence of the detection of ceramide trihexoside from a plant regenerated from a cell with a vector carrying the DNA encoding the protein as introduced therein.

The vector of the invention carries a promoter region enabling the expression of a foreign gene in an animal-, plant- or microbial cell. For example, promoters for constant gene expression in plant cells include those described below:

35S promoter of cauliflower mosaic virus (CaMV) (see for example, Odel et al., Nature, 313: 810, 1985; Dekeyser et al., Plant Cell, 2: 591, 1990: Terada and Shimamoto, Mol. GeN. Genet., 220: 389, 1990; and Benfey and Chua, Science, 250: 959-966, 1990), nopalin synthase promoter (An et al., Plant Physiol., 88: 547, 1988), octopin synthase promoter (Fromm et al., Plant Cell, 1: 977, 1989), and 2x CaMV/35S promoter with a translation enhancer sequence (Kay et al., Science, 236: 1299-1302, 1987).

Additionally, for example, promoters inducibly activated via extraneous stimulations can also be used for the expression of foreign genes in plant cells. Such promoter examples include those described below.

(a) Promoters induced by heat (Callis et al., Plant Physiol., 88: 965, 1988; Ainley et al., Plant Mol. Biol., 22: 13-23, 1993; and Gilmartin et al., The Plant Cell, 4: 839-949, 1992), (b) promoters induced optically (for example, pisum rbcS-3A promoter; Kuhlemeier et al., Plant Cell, 1: 471, 1989; and corn rbcS promoter; Schaffer & Shee N, Plant Cell, 3: 997, 1991), (c) promoters induced by hormones (for example, promoters induced by abscisic acid; Marcotte et al., Plant Cell. 1:471, 1989), (d) promoters induced by wounds (for example, potato PinII promoter; Keil et al., Nucl. Acids. Res. 14: 5641-5650, 1986, *Agrobacterium* mas promoter; Langridge et al., Bio/Technology 10: 305-308, 1989, and grape vst1 promoter; Weise et al., Plant Mol. Biol., 26: 667-677, 1994), and (e) promoters induced by chemical substances such as methyl jasmonate or salicylic acid (Gatz et al., Plant Mol. Biol., 48: 89-108, 1997).

Further, ubiquitin promoter, soybean Caulimoviridae SbCMV-like virus promoter, retrotransposon promoter, LHCPII promoter and the like can be utilized.

The vector of the invention can comprise for example an RNA processing signal such as intron positioned upstream or downstream the coding region of α1,4 GT. Additionally, the vector may comprise an additive regulation sequence derived from a non-translation region at the 3' terminus of a plant gene, such as the 3'-terminator region so as to enhance the stability of mRNA. Examples thereof include potato PI-II terminator region, or the 3'-terminator region of octopin synthase or nopalin synthase (NOS).

Furthermore, the vector of the invention may comprise a dominance-selective marker gene so as to allow rapid selection of the transformant. The dominance-selective marker gene includes for example antibiotic-resistant genes (for example, genes encoding resistance against hygromycin, kanamycin, bleomycin, G418, streptomycin or spectinomycin) and herbicide-resistant genes (for example, phosphinothricin acetyltransferase).

The cell types for introducing the vector therein preferably include tobacco, wheat, rice, corn, adzuki bean, and konjak. Any cell type may be used with no specific limitation to those described above, as long as the cell type can synthetically prepare lactosylceramide in the cell for allowing transformation.

The vector of the invention can be introduced in for example plant cells by methods known by a person skilled in the art. In case of introducing the vector in tobacco, for example, the above method includes for example the transformation method using *Agrobacterium* as described in an Example, the particle gun method, the electroporation method, the transformation method using monocotyledonous *Agrobacterium*, polycation method, and the transformation method of plant protoplast (polyethylene glycol method).

The *Agrobacterium* method can be used for gene introduction into for example rice (Hiei Y et al., Plant Mol. Biol., September; 35(1-2): 205-218), barley (Higuchi K et al., Plant J January; 25(2): 159-167), rapeseed plant (Damgaard O & Rasmussen O et al., Plant Mol. Biol., July 1991; 17(1) 1-8), potato (Yu J & Langridge & Transgenic Res., April 2003; 12(2): 163-169), asparagus (Ignacimuthu S Indian J Exp Biol., May 2000; 38(5): 493-498), eggplant (Rotino G L et al., Nat Biotechnol., December 1997; 15(13): 1398-1401), red pepper (Shin R. et al. Transgenic Res., April 2002; 11(2): 215-219), tomato, sweet potato and melon (as to all the three species, see Mihalka V. et al. Plant Cell Rep., April 2003; 21(8): 778-784), soybean (Zeng P et al. Plant Cell Rep., February 2004; 22(7) 478-482), sugar cane (Manickavasagam M et al. Plant Cell Rep., May 5, 2004), solgum (Zhao Z Y et al. Plant Mol. Biol., December 2000; 44(6): 789-798), Japanese noodle plant (soba) (Kojima M et al. Biosci Biotechnol Biochem. April 2000; 64(4): 845-847), carrot (Koyama H et al. Plant Cell Physiol May 1999; 40(5): 482-484), and apple (Szankowski I et al. Plant Cell Rep. September 2003; 22(2): 141-149).

Additionally, the electroporation or particle gun method can be utilized for gene introduction into for example rice (Shimamoto K et al. Nature, 338, 274-276 (1989)), and corn (Kyozuka J et al. Mol. Gen. Genet., August 228(1-2): 40-48). The particle gun method can be utilized for gene introduction into for example banana (Sagi L et al. Biotechnology (NY). May 1995; 13(5): 481-485) and rye (Popelka J C et al. Transgenic Res., October 2003; 12(5): 587-596).

The invention provides a transgenic plant cell with the vector introduced therein and with a possibility of regenerating a plant with a potency to generate ceramide trihexoside. The transgenic plant cell in accordance with the invention may be in any form as long as the cell is a plant cell with the vector introduced therein and with a potency to generate a plant or an aggregate of the cell. The plant cell in accordance with the invention includes for example cells from hanging drop culture, protoplast, leaf sections and callus.

The invention provides a plant with a potency to generate ceramide trihexoside as regenerated from the transgenic cell. The phrase "plant with a potency to generate ceramide trihexoside" means a plant modified so as to synthetically prepare ceramide trihexoside never synthetically prepared in plants via glycosyltransfer reactions from intrinsic lactosylceramide.

Additionally, the invention provides not only a plant regenerated from such cell with the vector introduced therein but also a progeny thereof or a clone thereof. Once a transgenic plant with the vector introduced into the genome thereof can be obtained, such progeny or clone can be obtained from the plant by sexual reproduction or asexual reproduction. Furthermore, a reproduction material (for example, seed, fruit, section, bulb, tuberous root, stock, callus, and protoplast) is obtained from the plant, a progeny thereof or a clone thereof, to produce the plant on the basis of the reproduction material at a mass scale.

In accordance with the invention, further, it is provided a method for producing a plant with a potency to generate ceramide trihexoside. The method includes a step of introducing the vector in a plant cell and a step of regenerating the plant from the vector-introduced cell.

The step of regenerating the plant from the transgenic plant cell can be done, depending on the plant type by a method known to a person skilled in the art. In case of tobacco, for example, the vector is allowed to infect tobacco by the leaf disk method as described below in Example 3; then, the tobacco leaves are washed with an MS culture broth containing hygromycin and carbenicillin as antibiotics so as to remove the bacterial cells used during the infection; continuously, the leaf is cultured in an MS agar culture medium with such antibiotics added therein for regeneration, to obtain the shoot of transgenic tobacco. Generally, the dominance-selective marker integrated in the vector for transformation gives antibiotic resistance to the germ of a transgenic plant. By exposing the germ to an appropriate concentration of an antibiotic, the resulting transformant can be screened. Antibiotics for use in the screening for the transformant include for example kanamycin and herbicides in addition to hygromycin. Other screening methods include MAT vector method.

Still further, the invention provides a method for producing ceramide trihexoside, including the use of the plant. Ceramide trihexoside can be recovered from the plant by a method known to a person skilled in the art. As one example, a method for extracting ceramide trihexoside from tobacco plant is described below.

First, total lipid is extracted from the plant with chloroform/methanol. Specifically, 5 to 10 g of tobacco leaves is immersed in 100 ml of chloroform:methanol (1:2/volume ratio), for disruption with a Polytron homogenizer for about 2 minutes. Then, the solution from such disruption is filtered through a miracloth(calbiochem) in four layers. The filtrate is transferred into a separation funnel, to which chloroform and water are added to a final volume ratio of chloroform:methanol:water being 1:1:0.9. The lower layer is recovered (two layers in separation), followed by concentration with a rotary evaporator, to extract total lipid.

Using the weak alkaline decomposition method, subsequently, sphingolipid is obtained from the total lipid fraction. Specifically, 30 ml of methanol containing 0.4M KOH is mixed with a part of the total lipid obtained by the method in a volume of about 0.5 ml (containing 0.8 g of total lipid), for reaction at 37° C. for 2 hours. During the period, only glycerolipid is decomposed but sphingolipid is never decomposed. The reaction solution is transferred into a separation funnel, to which 30 ml of chloroform and 27 ml of water are added. After mixing the solution together, then, the lower layer (two layers in separation) is recovered, for concentration of the layer with a rotary evaporator, to obtain a fraction of sphingolipid.

Finally, ceramide trihexoside is purified, by using a silica gel column. Specifically, silica gel is packed in a glass column of an inner diameter of 2 cm for chromatography to a height of 1.5 cm. Sphingolipid dissolved in 0.5 ml of chloroform: methanol (90:10) is loaded onto the column, while the chloroform:methanol solution is modified from the ratio of 90:10 to 70:30 on a gradient. First, a pigment and glycosylceramide are eluted. Continuously, lactosylceramide is eluted on a ratio of about 80:20. Immediately thereafter, ceramide trihexoside is eluted. Ceramide trihexoside obtained by such method is also included within the scope of the invention.

In accordance with the invention, the following advantages can be exerted: (1) ceramide trihexoside can be synthetically prepared at a state without any risk of animal-derived infections, at a mass scale, using a recombinant plant; (2) this indicates that the introduction of two or more glycosyltransferase genes into biological organisms enables complex sugar chain modifications of lipid and protein; (3) although ceramide trihexoside essentially never generated in plants is sphingoglycolipid intrinsic to animals, ceramide trihexoside can now be produced in plants so that sphingoglycolipid intrinsic to animals can be produced at a mass scale at low cost, of which the production has involved much difficulty due to the cost and safety problems despite the industrial usefulness; (4) the method of the invention is excellent in terms of safety profile because the method uses plants during the production; and (5) a technique for extending the biological sugar chains of a lipid and a protein in animal-, plant- or microbial cells is provided.

The invention is now specifically described in the following Examples. However, the invention is never limited by these Examples.

EXAMPLE 1

Method for Isolating Human-Derived α1,4-galactosyltransferase Gene (α1,4GT)

Using human heart-derived polyA$^+$ mRNA (STRATAGENE) as template and oligo dT primer, the first strand cDNA was synthetically prepared by reverse transcription. Using the cDNA as template, the full-length ORF (1,062 bp) of the gene corresponding to α1,4GT (accession No. AB037883 (NCBI)) was amplified by the PCR method. For the PCR, a14GT/27F (5'-ATGTCCAAGCCCCCCGAC-CTCCTGCTG-3'/SEQ ID NO: 3) and a14GT/27R (5'-TCA-CAAGTACATTTTCATGGCCTCGTG-3'/SEQ ID NO: 4) were used as primers. KOD Plus DNA polymerase (TOYOBO) was used for PCR. PCR cycle was done at 94° C. for 2 minutes, followed by 35 times of a cycle of 94° C. for 15 seconds and 68° C. for 2 minutes. The resulting single band was inserted into the EcoRV site of a plasmid pBluescript II KS+, to obtain a pBS/α14GT clone. The sequence of the cDNA clone was verified by the determination of restriction enzyme sites and sequencing by using ABI PRISM Big Dye Terminator Ver3 (Applied Biosystems, California, USA). The DNA sequence (1062 bp) of human α1,4GT and the amino acid sequence (353 amino acids) encoded by the DNA sequence are shown as SEQ ID NOS: 1 and 2, respectively.

EXAMPLE 2

GUS Cartridge Removal from Ti Plasmid pIG121Hm and Addition of Restriction Enzyme Sites Ti plasmid vector pIG121Hm was digested with restriction enzymes XbaI and SacI and then fractionated by electrophoresis, to obtain a fragment pIG121HmΔGUS from which the GUS cartridge was removed. An adapter with restriction enzyme sites with SpeI, XhoI, NotI and SacI was inserted therein. The double-stranded DNA composing the adapter comprises (5'-CATGTACTAGTCTCGAGGCGGCCGC-GAGCT-3'/SEQ ID NO: 5) and (5'-CGCGGCCGCCTC-GAGACTAGTA-3'/SEQ ID NO: 6). In such manner, Ti plasmid pIG121Hm/Adaptor was obtained.

EXAMPLE 3

Construction of Expression Vector of Human-Derived α1,4GT for Plants

Figure 1:
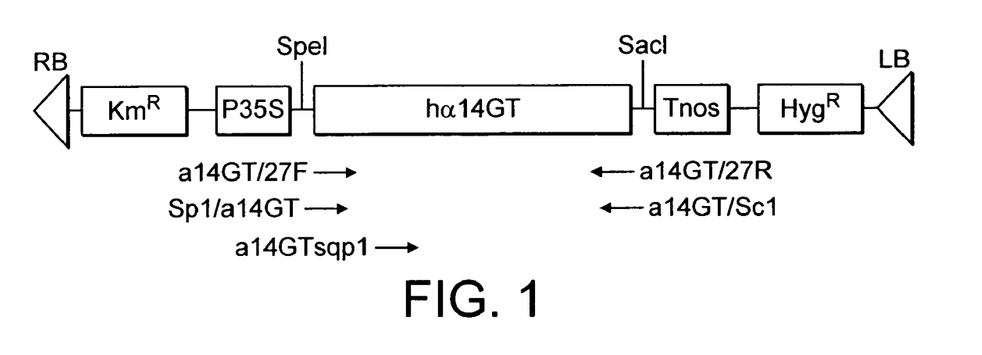

So as to insert the ORF of α1,4GT in pIG121Hm/Adaptor, PCR for the addition of restriction enzyme sites with SpeI and SacI was done. Using Sp1/a14 (5'-TTGACTAGTATGTC-CAAGCCCCCCGACCTC-3'/SEQ ID NO: 7) and a14/Sc1 (5'-AAGGAGCTCTCACAAGTACATTTTCATGGC-3'/ SEQ ID NO: 8) as primers, the reaction was done under the same conditions as described above. The resulting PCR product was digested with SpeI and SacI, and ligated with SpeI- and SacI-digested pIG121Hm/Adaptor fragments, to construct an expression vector pIG121Hm/α14GT for plants. The clone was sequenced by the same method as described above, to confirm the absence of miss-match. The expression of the inserted α1,4GT cDNA is structurally regulated by cauliflower mosaic virus 35S promoter (35S) and nopalin synthase terminator (NOS). Additionally, the cDNA contains the hygromycin resistant gene as a transformant selective marker. The expression vector of human α1,4GT for plants is shown in FIG. 1.

EXAMPLE 4

Tobacco Transformation

Lactosylceramide producing tobacco (Nicotiana tabacum cv. Blight Yellow) (as taught in PCT/JP2005/015899 (Publication No. WO 2006/025443).) was transformed using *Agrobacterium* by the leaf disk method. From a tobacco leaf aseptically grown, a leaf disk of one side of about 1 cm was scissored out and then immersed in a bacterial solution of *Agrobacterium tumefaciens* strain LBA4404 containing pIG121Hm/α14GT for 2-day concurrent culturing on an MS agar culture medium for infection. On day 3, the leaf disk was washed with an MS culture broth containing 5 mg/l hygromycin and 500 mg/l carbenicillin to remove *Agrobacterium* cells. Then, the leaf disk was cultured in an MS agar culture medium with these antibiotics added thereto, to obtain a shoot of transgenic tobacco.

EXAMPLE 5

Analysis of Genome DNA of Recombinant Tobacco with α1,4GT Introduced therein

So as to verify the insertion of human α1,4GT in the chromosomal genome of tobacco, PCR was done. DNA was extracted from about 0.1 g of the leaves of recombinant tobacco with verified hygromycin resistance (DNEASY Plant Mini Kit, QIAGEN). Using a part thereof as template, PCR was done. As primers, a14GT/27F and a14GT/27R were used so as to contain the full-length ORF of α1,4GT. For PCR, TAKARA EX Taq polymerase was used. A cycle of 94° C. for 30 seconds, 65° C. for 30 seconds and 72° C. for 1.5 minutes was repeated 40 times. Six clones were examined. A band corresponding to α1,4-galactosyltransferase gene appeared in four of the clones. It was confirmed that the gene was inserted in the nuclear genome.

Figure 2:
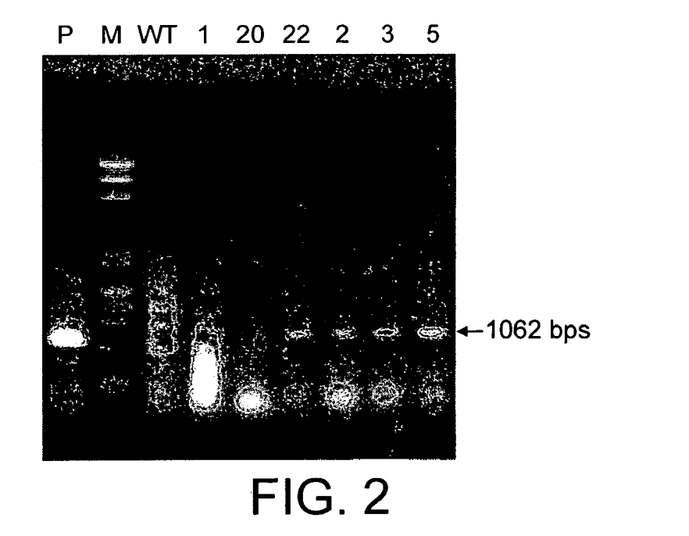
FIG. 2 is a photographic picture of PCR analysis using the genome DNA of transgenic tobacco as template. P represents positive control using pIG121Hm/α14GT as PCR template; M represents electrophoresis markers λ/Hind III digest and φX174/HaeIII digest; WT represents the wild strain; Nos. 1, 20, 22, 2, 3, and 5 individually represent clone numbers of gene recombinant tobacco.

The PCR results are shown in FIG. 2.

EXAMPLE 6

Analysis of Recombinant Tobacco RNA with α1,4GT Introduced therein

Figure 3:
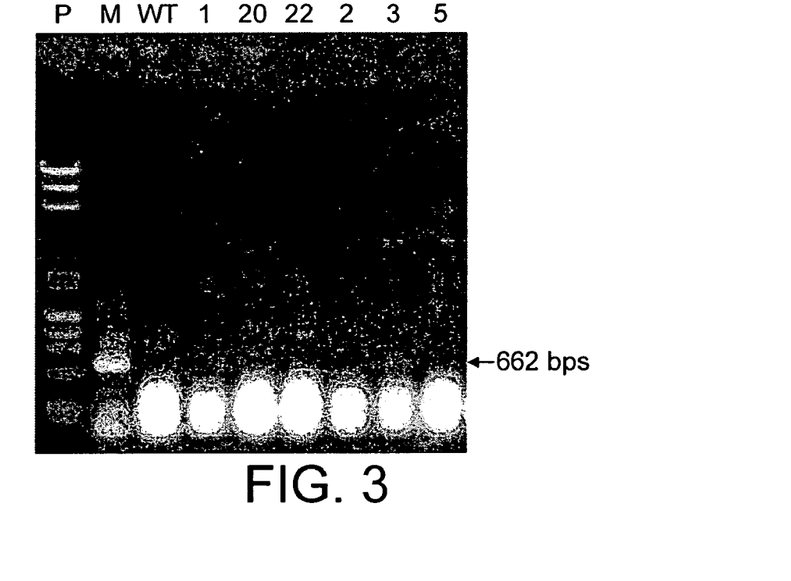
FIG. 3 is a photographic picture of RT-PCR analysis using transgenic tobacco RNA as template. P represents positive control using pIG121Hm/α14GT as PCR template; M represents electrophoresis markers λ/Hind III digest and φX174/HaeIII digest; WT represents the wild strain; Nos. 1, 20, 22, 2, 3, and 5 individually represent clone numbers of gene recombinant tobacco.

So as to verify the expression of human α1,4GT mRNA in the tobacco, RT-PCR was done. Total RNA was extracted from about 0.1 g of the leaves of the recombinant tobacco with certified hygromycin resistance (RNEASY Plant Mini Kit, QIAGEN). Using a part thereof as template, PCR was done. As primers, a14GTsqp1 (5'-GCTGCTTCCCGAAT-GTCCAG/SEQ ID NO: 9) and a14GT/27R were used. For RT-PCR, Ready-To-Go RT-PCR Beads (Amersham) was used, for reverse transcription at 42° C. for 30 minutes and subsequent treatment at 95° C. for 5 minutes, to inactivate the enzyme. Then, for PCR, a cycle of 95° C. for 30 seconds, 55° C. for 30 seconds and 72° C. for 2 minutes was repeated 40 times. Six clones were examined. A band corresponding to α1,4GT appeared in one of the clones. It was confirmed that the RNA was surely transcribed. The results of RT-PCR are shown in FIG. 3.

EXAMPLE 7

Lipid Analysis of Recombinant Tobacco

After about 10 g of tobacco leaves was cut into a square piece of about 1 cm, 100 ml of chloroform/methanol (1:2) was added for disruption with Polytron homogemizer for one minute. The resulting solution was filtered under aspiration through a miracloth in four layers in a Buchner funnel, to which chloroform and water were added for partition into two layers according to the Bligh-Dyer method, to recover the chloroform layer. After the layer was dried under reduced pressure, the dried product was dissolved in 1 ml of chloroform/methanol (2:1) to prepare a total lipid fraction.

So as to obtain sphingolipid, the total lipid fraction was decomposed with a weak alkali, to decompose and remove glycerolipid. 10 ml of 0.4M KOH methanol solution was added to the total lipid, for reaction at 37° C. for 2 hours. Chloroform and water were added to the reaction mixture, for partition into two layers, to recover an alkali-resistant lipid. The resulting lipid was then dried under reduced pressure, to dissolve a small amount of chloroform/methanol (2:1) to prepare an alkali-resistant lipid enriched with total sphingolipid.

EXAMPLE 8

Identification of Ceramide Trihexoside Fractionated by TLC

Figure 4:
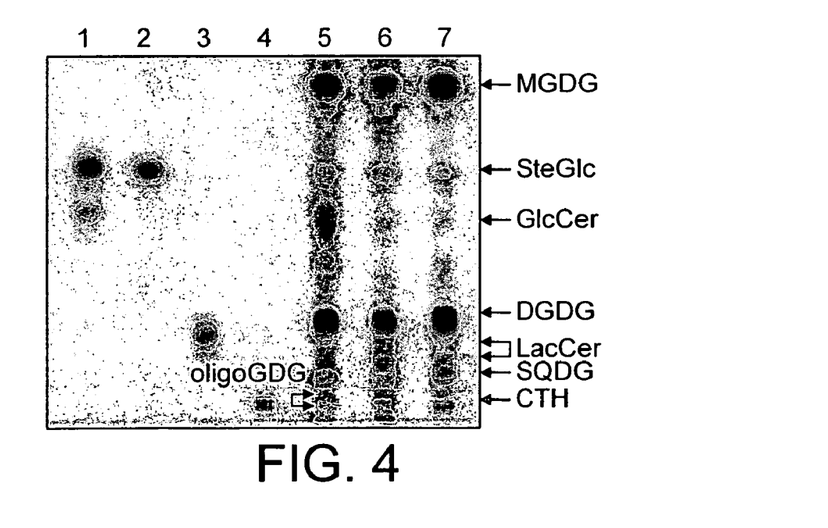
Figure 5:
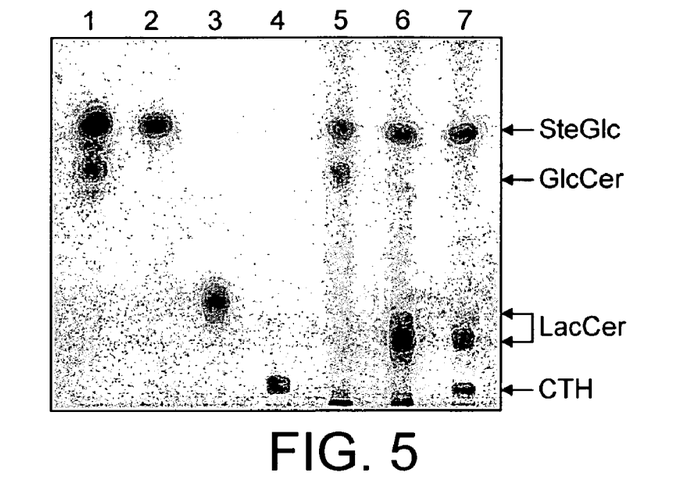

So as to separate the lipid into lipid classes, the lipid was applied to silica gel TLC. The total sphingolipid fraction was loaded onto silica gel TLC, for development with chloroform/methanol/water (65:16:1) as a developing solvent. The lipid was detected with the primuline and the orcinol sulfate method. Consequently, newly synthesized ceramide trihexoside was confirmed. A TLC photographic picture of the total lipid is shown in FIG. 4. A TLC photographic picture of the alkali-resistant lipid is shown in FIG. 5.

EXAMPLE 9

Analysis of Sugar Chain of Ceramide Trihexoside

Figure 6:
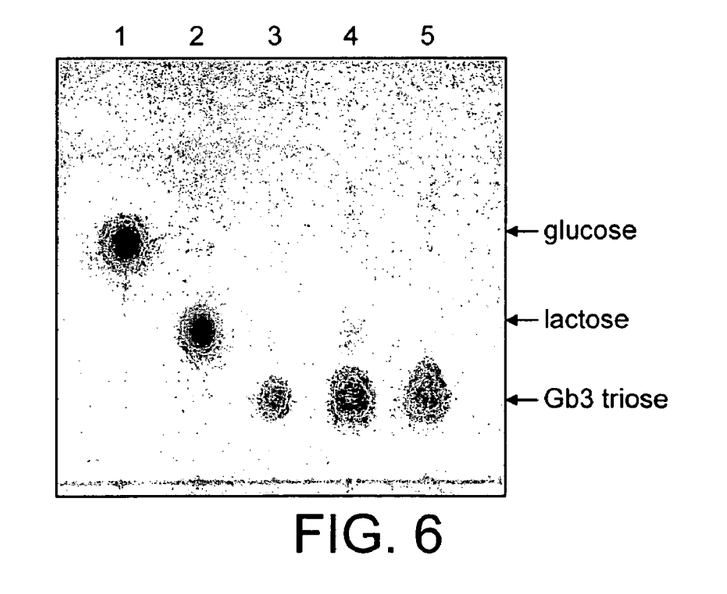
FIG. 6 represents a photographic picture of the sugar chain analysis of the ceramide trihexoside of transgenic tobacco. 1 represents glucose standard sample; 2 represents lactose standard sample; 3 represents Gb3 triose standard sample; 4 represents CTH-derived sugar chain purified from α14GT tobacco; 5 represents sugar chain derived from ceramide trihexoside standard sample.

The resulting ceramide trihexoside was separated and recovered from TLC, for the analysis of the sugar chain structure. The ceramide trihexoside was dissolved in 25 mM ammonium acetate buffer, pH 5.0 and 0.4% Triton X-100, for cleaving the sugar chain with endoglycoceramidase 2 (rEG-Case II, Takara) for TLC development. It was confirmed that the sugar chain structure was Gb3 triose (Galα1-4Galβ1-4Glc). The TLC photographic picture is shown in FIG. 6.

EXAMPLE 10

TOF-Mass Analysis of Ceramide Trihexoside

Figure 7:
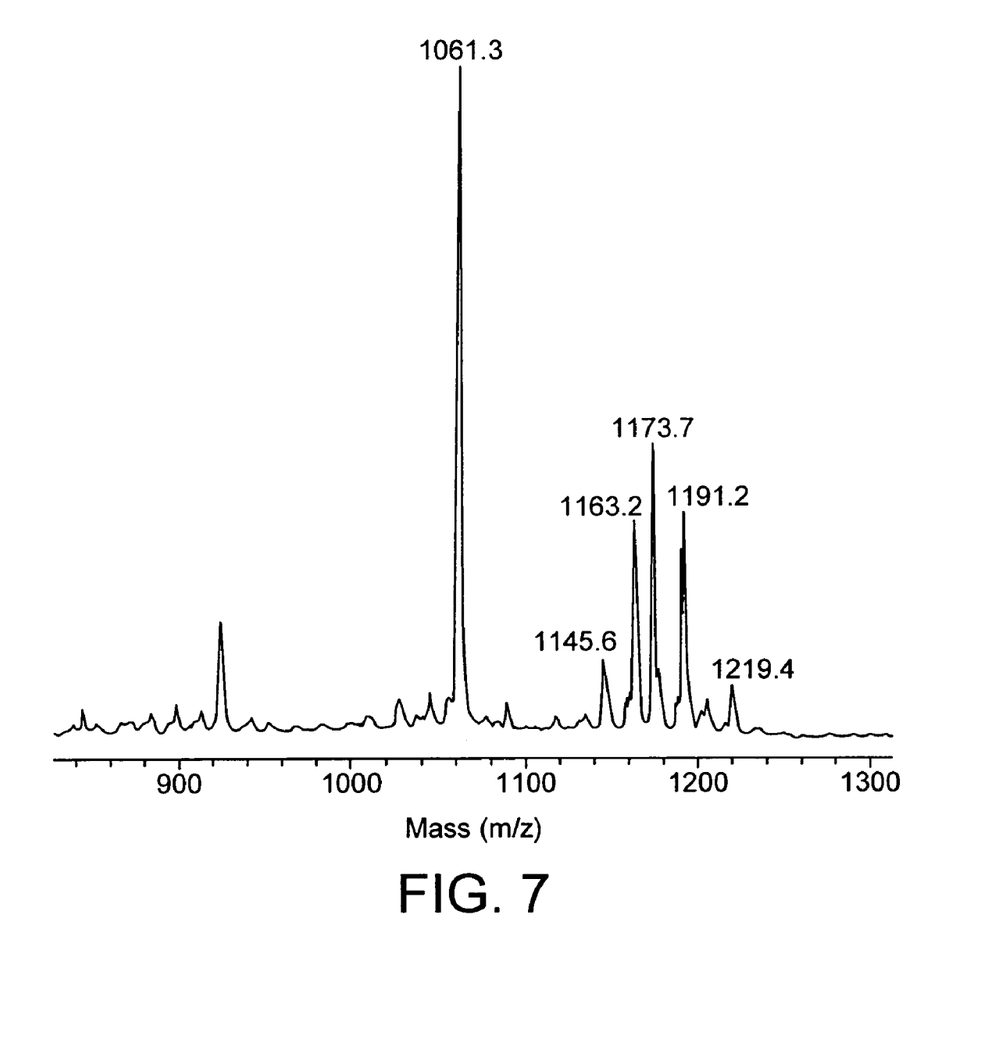
FIG. 7 showes a TOF-mass spectrograph of ceramide trihexoside of transgenic tobacco expressing human-derived α1,4GT gene.
Figure 8:
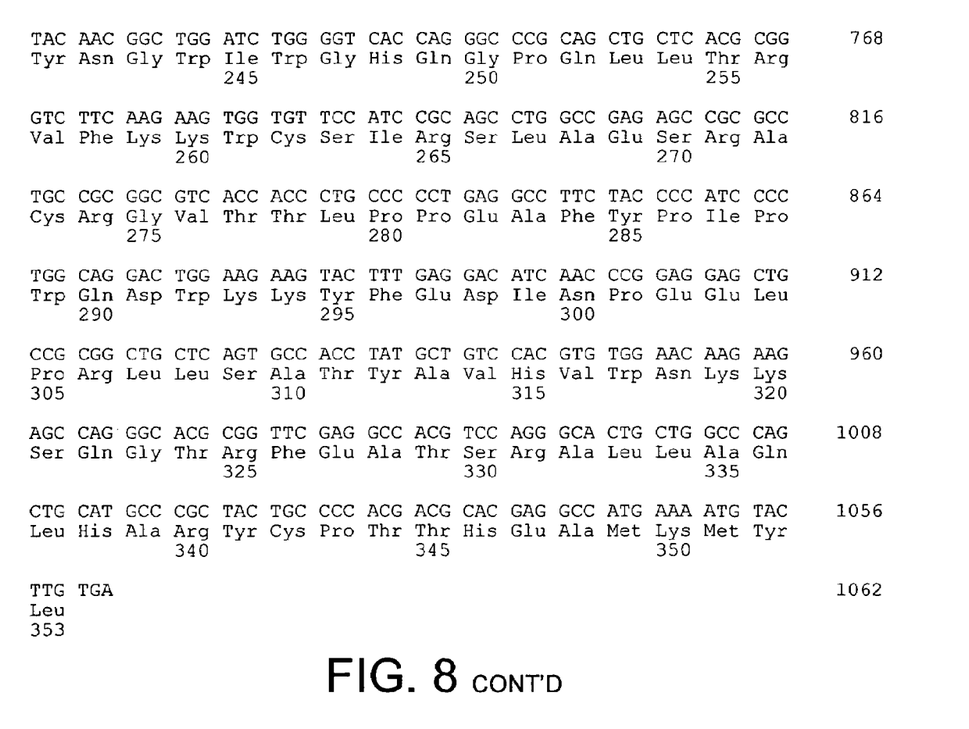
FIG. 8 represents the DNA sequence (1-1062) (SEQ ID NO: 1) and amino acid sequence (1-353) (SEQ ID NO:2) of human α1,4GT. The sequence is split between 2 pages, the first showing nucleotides 1-720 and the second showing nucleotides 721-1062.
Figure 9:
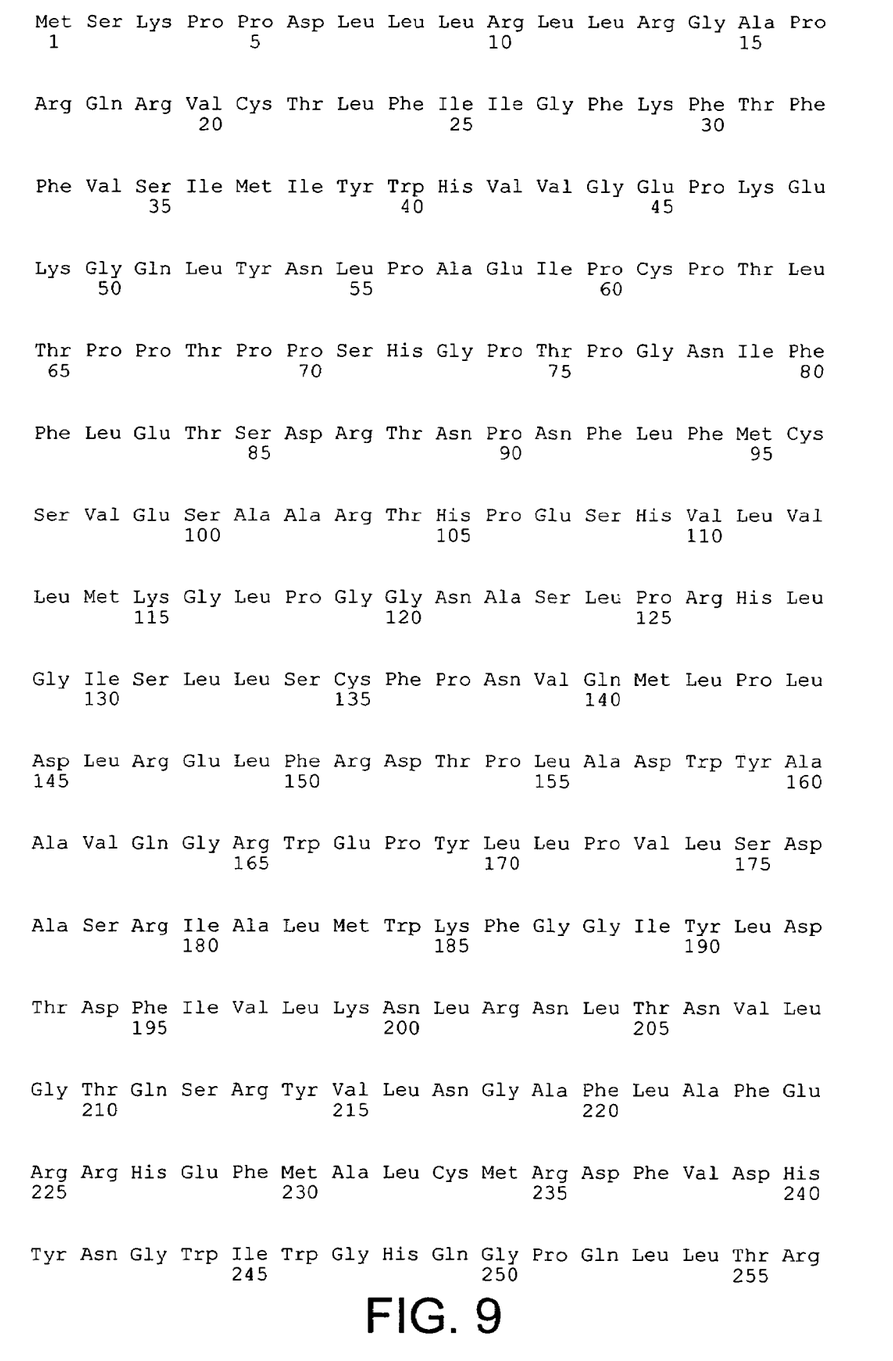
FIG. 9 represents the amino acid sequence (1-353) of human α1,4GT (SEQ ID NO: 2). The sequence is split between 2 pages the first showing amino acids 1-256 and the second showing amino acids 257-353.

The resulting ceramide trihexoside was mixed with 2,5-dihydroxybenzoic acid (DHB). The resulting mixture was dried up, for analysis with MALDI-TOF-mass (AutoFLEX II-SH TOF/TOF, Bulker Daltonics). A peak corresponding to the ceramide trihexoside molecule was detected. The chromatogram by TOFF-MAS is shown in FIG. 7. The ceramide trihexoside molecule species corresponding to the individual peaks are shown in Table 3.

EXAMPLE 11

Analysis of Ceramide Trihexoside Content

The sphingolipid separated by TLC was developed by the orcinol sulfate, to assay the content of ceramide trihexoside by densitometry. The intensity of orcinol by TLC as shown in FIG. 4 was read with a densitometer, to assay the individual lipids to analyze the relative amount of each lipid and the absolute amount of ceramide trihexoside. The compositions of glycolipids are shown in Table 1, while the content of ceramide trihexoside is shown in Table 2.

TABLE 1

| Composition of glycolipid in tobacco leaves (% by weight) | Wild strain | Human α1,4GT recombinant tobacco |
|---|---|---|
| Monogalactosyldiacylglycerol | 43.8 (±0.3) | 39.5 (±0.8) |
| Digalactosyldiacylglycerol | 43.8 (±1.0) | 42.7 (±0.8) |
| Sulfoquinobosyldiacylglycerol | 4.0 (±0.4) | 3.3 (±0.3) |
| Sterylglucoside | 3.8 (±0.5) | 2.7 (±0.2) |
| Glucosylceramide | 4.5 (±0.5) | 0.9 (±0.1) |
| Lactosylceramide | 0 (±0) | 2.5 (±0.2) |
| Ceramide trihexoside | 0 (±0) | 8.9 (±0.1) |
| Oligogalactosyldiacylglycerol | tr | Tr |

Mean (± standard deviation)
The results with the wild strain are shown from quadruplicate experiments, while the results with the recombinant tobacco are shown from sextet experiments: tr (<0.4%)

TABLE 2

Ceramide trihexoside content of tobacco leaves (μg/g leaves)

| | |
|---|---|
| Wild strain | 0 (±0) |
| Human α1,4GT recombinant tobacco | 66.5 (±8.5) |

Mean (± standard deviation)
Results from sextet experiments

Consequently, the recombinant tobacco with human α1,4GT introduced therein contained about 67 μg of lactosylceramide per 1 g of fresh leaves.

TABLE 3

Individual peaks measured by MALDI-TOF mass and ceramide trihexoside molecule species corresponding to the peaks

| Peak position | (m/z) Assignment of molecular mass (calculated) |
|---|---|
| 1061.3 | d18:2-C16:0 + K (1061.4) |
| 1145.6 | d18:2-C22h:0 + Na (1145.5) |
| 1163.2 | d18:0-C23h:0 + Na (1163.5) |
| 1173.7 | d18:2-C24h:0 + Na (1173.5) |
| 1191.2 | t18:1-C24h:0 + Na (1191.5) |
| | d18:0-C25h:0 + Na (1191.6) |
| 1219.4 | t18:1-C26h:0 + Na (1219.6) |

The inventors previously introduced a single one of β1,4-galactosyltransferase gene (Accession No. AF097159 (NCBI)) (as taught in WO2006/025443) as a glycosyltransferase gene into tobacco to synthetically prepare lactosylceramide to successfully generate 200 μg or more of lactosylceramide per 1 g of fresh leaves. In accordance with the invention, further, a second glycosyltransferase gene was successfully introduced into tobacco to add a new sugar at the third position from ceramide to generate ceramide trihexoside. As described above, the use of the approach for introducing two or more plural glycosyltransferase genes into a cell enables the generation of a lipid or a protein with various sugar chain modifications. Thus, the approach is very useful.

As described above in detail, the invention relates to a technique for extending the biological sugar chain of a lipid or a protein in animal-, plant- or microbial cells. In accordance with the invention, the introduction of two or more glycosyltransferase genes into biological organisms enables sugar modifications of lipids or proteins. Sphingoglycolipids intrinsic to animals, which were previously produced with much difficulty due to the cost or safety problems although such lipids are industrially useful, can be produced at a mass scale in an inexpensive manner without any risk of animal-derived infections.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What is claimed is:

1. A transgenic plant cell transformed with a nucleic acid comprising a promoter that functions in plants operably linked to a polynucleotide encoding human β1,4-galactosyltransferase (β1,4 GT5) and a nucleic acid comprising a promoter that functions in plants operably linked to a polynucleotide a human α1,4-galactosyltransferase wherein said plant cell produces ceramide trihexoside.

2. A transgenic plant cell transformed with a nucleic acid comprising a promoter that functions in plants operably linked to a polynucleotide encoding human β1,4-galactosyltransferase (β1,4 GT5) that converts glucosylceramide present in the plant into lactosylceramide and a nucleic acid comprising a promoter that functions in plants operably linked to a polynucleotide encoding a human α1,4-galactosyltransferase which converts the lactosylceramide into ceramide trihexoside.

3. The transgenic plant cell of claim 1, wherein the polynucleotide encoding the human α1,4-galactosyltransferase has the sequence set forth in SEQ ID NO:1.

4. The transgenic plant cell of claim 1, wherein the human α1,4-galactosyltransferase has the amino acid sequence set forth in SEQ ID NO:2.

5. The transgenic plant cell according claim 1, wherein the polynucleotides are human- or animal-derived.

6. A plant that generates ceramide trihexoside as regenerated from the transgenic plant cell according to claim 1.

7. A plant that generates ceramide trihexoside as regenerated from the transgenic plant cell according to claim 5.

8. A plant that generates ceramide trihexoside, which is a progeny of the plant according to claim 6 or a clone thereof.

9. A plant that generates ceramide trihexoside, which is a progeny of the plant according to claim 7 or a clone thereof.

10. A reproduction material of the plant that generates ceramide trihexoside according to claim 6; wherein the reproduction material comprises the polynucleotides.

11. A reproduction material of the plant that generates ceramide trihexoside according to claim 7; wherein the reproduction material comprises the polynucleotides.

12. A reproduction material of the plant that generates ceramide trihexoside according to claim 8; wherein the reproduction material comprises the polynucleotides.

13. A reproduction material of the plant that generates ceramide trihexoside according to claim 9; wherein the reproduction material comprises the polynucleotides.

14. A method for producing a plant that generates ceramide trihexoside, including a step of making a transgenic plant cell by introducing a nucleic acid comprising a promoter that functions in plants overably linked to a polynucleotide encoding human β1,4-galactosyltransferase (β1,4GT5) that converts glucosylceramide present in the plant into lactosylceramide and a nucleic acid comprising a promoter that functions in plants operably linked to a polynucleotide encoding a human α1,4-galactosyltransferase which converts the lactosylceramide into ceramide trihexoside into a plant cell, and a step of regenerating a plant from the transgenic plant cell.

15. A method for producing ceramide trihexoside including growing a plant according to claim 6 to synthetically prepare ceramide trihexoside.

16. A method for producing ceramide trihexoside including growing a plant according to claim 7 to synthetically prepare ceramide trihexoside.

17. A method for producing ceramide trihexoside including growing a plant according to claim 8 to synthetically prepare ceramide trihexoside.

18. A method for producing ceramide trihexoside including growing a plant according to claim 9 to synthetically prepare ceramide trihexoside.

* * * * *

SEQUENCE LISTING

<160> NUMBER OF SEQ ID NOS: 9

<210> SEQ ID NO 1
<211> LENGTH: 1062
<212> TYPE: DNA
<213> ORGANISM: Homo sapiens

<400> SEQUENCE: 1

```
atgtccaagc cccccgacct cctgctgcgg ctgctccggg gcgcccaag gcagcgggtc      60 tgcaccctgt tcatcatcgg cttcaagttc acgttttcg tctccatcat gatctactgg     120
cacgttgtgg gagagcccaa ggagaaaggg cagctctata acctgccagc agagatcccc     180
tgccccacct tgacaccccc cacccacacc tcccacggcc ccactccagg caacatcttc     240
ttcctggaga cttcagaccg gaccaacccc aacttcctgt tcatgtgctc ggtggagtcg     300
gccgccagaa ctcaccccga atcccacgtg ctggtcctga tgaaagggct tccgggtggc     360
aacgcctctc tgccccggca cctgggcatc tcacttctga gctgcttccc gaatgtccag     420
atgctcccgc tggacctgcg ggagctgttc cgggacacac ccctggccga ctggtacgcg     480
gccgtgcagg ggcgctggga gccctacctg ctgcccgtgc tctccgacgc ctccaggatc     540
gcactcatgt ggaagttcgg cggcatctac ctggacacgg acttcattgt tctcaagaac     600
ctgcggaacc tgaccaacgt gctgggcacc cagtcccgct acgtcctcaa cggcgcgttc     660
ctggccttcg agcgccggca cgagttcatg gcgctgtgca tgcgggactt cgtggaccac     720
tacaacggct ggatctgggg tcaccagggc ccgcagctgc tcacgcgggt cttcaagaag     780
```

-continued

```
tggtgttcca tccgcagcct ggccgagagc cgcgcctgcc gcggcgtcac caccctgccc    840
cctgaggcct tctaccccat ccctggcag gactggaaga agtactttga ggacatcaac    900
ccggaggagc tgccgcggct gctcagtgcc acctatgctg tccacgtgtg gaacaagaag    960
agccagggca cgcggttcga ggccacgtcc agggcactgc tggcccagct gcatgcccgc   1020
tactgcccca cgacgcacga ggccatgaaa atgtacttgt ga                      1062
```

<210> SEQ ID NO 2
<211> LENGTH: 353
<212> TYPE: PRT
<213> ORGANISM: Homo sapiens

<400> SEQUENCE: 2

```
Met Ser Lys Pro Pro Asp Leu Leu Arg Leu Leu Arg Gly Ala Pro
1               5                   10                  15

Arg Gln Arg Val Cys Thr Leu Phe Ile Ile Gly Phe Lys Phe Thr Phe
            20                  25                  30

Phe Val Ser Ile Met Ile Tyr Trp His Val Val Gly Glu Pro Lys Glu
        35                  40                  45

Lys Gly Gln Leu Tyr Asn Leu Pro Ala Glu Ile Pro Cys Pro Thr Leu
    50                  55                  60

Thr Pro Pro Thr Pro Pro Ser His Gly Pro Thr Pro Gly Asn Ile Phe
65                  70                  75                  80

Phe Leu Glu Thr Ser Asp Arg Thr Asn Pro Asn Phe Leu Phe Met Cys
                85                  90                  95

Ser Val Glu Ser Ala Ala Arg Thr His Pro Glu Ser His Val Leu Val
            100                 105                 110

Leu Met Lys Gly Leu Pro Gly Gly Asn Ala Ser Leu Pro Arg His Leu
        115                 120                 125

Gly Ile Ser Leu Leu Ser Cys Phe Pro Asn Val Gln Met Leu Pro Leu
    130                 135                 140

Asp Leu Arg Glu Leu Phe Arg Asp Thr Pro Leu Ala Asp Trp Tyr Ala
145                 150                 155                 160

Ala Val Gln Gly Arg Trp Glu Pro Tyr Leu Leu Pro Val Leu Ser Asp
                165                 170                 175

Ala Ser Arg Ile Ala Leu Met Trp Lys Phe Gly Gly Ile Tyr Leu Asp
            180                 185                 190

Thr Asp Phe Ile Val Leu Lys Asn Leu Arg Asn Leu Thr Asn Val Leu
        195                 200                 205

Gly Thr Gln Ser Arg Tyr Val Leu Asn Gly Ala Phe Leu Ala Phe Glu
    210                 215                 220

Arg Arg His Glu Phe Met Ala Leu Cys Met Arg Asp Phe Val Asp His
225                 230                 235                 240

Tyr Asn Gly Trp Ile Trp Gly His Gln Gly Pro Gln Leu Leu Thr Arg
                245                 250                 255

Val Phe Lys Lys Trp Cys Ser Ile Arg Ser Leu Ala Glu Ser Arg Ala
            260                 265                 270

Cys Arg Gly Val Thr Thr Leu Pro Pro Glu Ala Phe Tyr Pro Ile Pro
        275                 280                 285

Trp Gln Asp Trp Lys Lys Tyr Phe Glu Asp Ile Asn Pro Glu Glu Leu
    290                 295                 300

Pro Arg Leu Leu Ser Ala Thr Tyr Ala Val His Val Trp Asn Lys Lys
305                 310                 315                 320

Ser Gln Gly Thr Arg Phe Glu Ala Thr Ser Arg Ala Leu Leu Ala Gln
```

|     |     |     |     | 325 |     |     |     |     | 330 |     |     |     |     | 335 |
| --- | --- | --- | --- | --- | --- | --- | --- | --- | --- | --- | --- | --- | --- | --- |
| Leu | His | Ala | Arg | Tyr | Cys | Pro | Thr | Thr | His | Glu | Ala | Met | Lys | Met | Tyr |
|     |     |     | 340 |     |     |     |     | 345 |     |     |     |     | 350 |

Leu

<210> SEQ ID NO 3
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 3
atgtccaagc ccccgacct cctgctg                                         27

<210> SEQ ID NO 4
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 4
tcacaagtac attttcatgg cctcgtg                                        27

<210> SEQ ID NO 5
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 5
catgtactag tctcgaggcg gccgcgagct                                     30

<210> SEQ ID NO 6
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 6
cgcggccgcc tcgagactag ta                                             22

<210> SEQ ID NO 7
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 7
ttgactagta tgtccaagcc ccccgacctc                                     30

<210> SEQ ID NO 8
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 8
aaggagctct cacaagtaca ttttcatggc                                     30

-continued

```
<210> SEQ ID NO 9
<211> LENGTH: 20
<212> TYPE: DNA
<213> ORGANISM: Artificial
<220> FEATURE:
<223> OTHER INFORMATION: An artificially synthesized primer sequence
<400> SEQUENCE: 9
gctgcttccc gaatgtccag                                              20
```